United States Patent [19]

Pinol et al.

[11] Patent Number: 5,128,343

[45] Date of Patent: Jul. 7, 1992

[54] DERIVATIVES OF PYRIMIDINYL-PIPERAZINYL-ALKYL AZOLES WITH ANXIOLYTIC AND/OR TRANQUILIZING ACTIVITY

[75] Inventors: Augusto C. Pinol; Jordi F. Constansa; Juan P. Corominas, all of Barcelona, Spain

[73] Assignee: Laboratorios del Dr. Esteve, Barcelona, Spain

[21] Appl. No.: 476,815

[22] Filed: Feb. 7, 1990

[30] Foreign Application Priority Data

Feb. 9, 1989 [FR] France .................. 89 01700

[51] Int. Cl.⁵ .................. A61K 31/505; C07D 403/14
[52] U.S. Cl. .................. 514/252; 544/295
[58] Field of Search .................. 544/295; 514/252

[56] References Cited

U.S. PATENT DOCUMENTS 4,367,335  1/1983  Temple, Jr. et al. .............. 544/295
4,487,773  12/1984 Temple, Jr. et al. .............. 544/295
4,547,499  10/1985 Hester, Jr. .............. 514/235
4,675,403  6/1987  Abou-Gharbia et al. .......... 544/295

FOREIGN PATENT DOCUMENTS 129128 12/1984 European Pat. Off. .

OTHER PUBLICATIONS

European Journal of Medicinal Chemistry, vol. 22, No. 4, Jul.-Aug. 1987, pp. 337-345.

Primary Examiner—Jane T. Fan
Assistant Examiner—James H. Turnipseed
Attorney, Agent, or Firm—Dressler, Goldsmith, Shore, Sutker & Milnamow, Ltd.

[57] ABSTRACT

The present invention relates to heterocyclic compounds characterized in that they correspond to the general formula I:

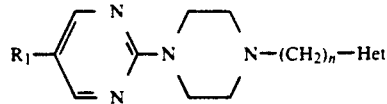

in which $R_1$ represents a hydrogen atom or a halogen, n can have the values 1 to 6 and Het represents an azole, or one of its derivatives selected from among imidazole, indazole, tetrahydroindazoles, pyrazole or pyrazoline and which can be represented by the general formula II:

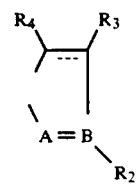

in which A and B, always different, represent a carbon atom or a nitrogen atom, the dashed line indicates the possible presence of a double bond between positions 4 and 5, and $R_2$, $R_3$ and $R_4$, identical or different, and can also form a part of another ring, aromatic or not, represent a hydrogen atom, a halogen, a lower alkyl radical, a nitro radical, a hydroxyl radical, an oxo radical, an alkoxy radical, a cyano radical, a carboxylic radical, a carboxamido radical, an alkyl carboxylate radical, an aryle or substituted aryl radical, or an amino radical, of general formula III:

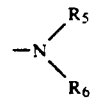

in which $R_5$ and $R_6$, identical or different, represent a hydrogen atom, an alkyl radical, an aryl radical, a heteroaryl radical, an alkenyl radical, an alkylcarboxy radical, an arylcarboxy radical, an alkylsulfonyl radical or an arylsulfonyl radical.

4 Claims, No Drawings

DERIVATIVES OF PYRIMIDINYL-PIPERAZINYL-ALKYL AZOLES WITH ANXIOLYTIC AND/OR TRANQUILIZING ACTIVITY

BACKGROUND OF THE INVENTION

The present invention relates to novel derivatives of 1H-azole-($\omega$-(4-(2-pyrimidinyl)-1-piperazinyl)alkyl), their process of preparation, as well as their use as medicaments.

The compounds according to the present invention may be used in the pharmaceutical industry as intermediates and for the preparation of medicaments.

1-4-(2-pyrimidinyl-1-piperazinyl)-butyl-N-heterocyclyl-diones are already known, for example: Wu Y. H. et al *J Med Chem* 1969, 12, 876, Wu Y. H. et al *J Med Chem* 1972, 15, 477; Temple D. L. et al U.S. Pat. No. 4,456,756; Yevich J. P. et al *J Med Chem* 1983, 26, 194, but on the other hand examples with azoles have not been found.

We have now discovered that the novel derivatives of 1H-azole-($\omega$-(4-(2-pyrimidinyl)-1-piperazinyl)alkyl), which form the subject of the present invention, show biological activity on the central nervous system; in particular they show anxiolytic and tranquilizing activities, enabling their use in therapeutics in the treatment of anxiety.

GENERAL DESCRIPTION OF THE INVENTION

The compounds according to the present invention correspond to the general formula I:

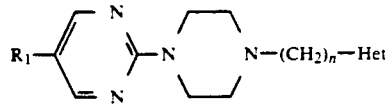

in which $R_1$ represents a hydrogen atom or a halogen, n may have the values 1 to 6 and Het represents an azole or one of its derivatives, selected from among imidazole, indazole, tetrahydroindazoles and pyrazole which may be represented by the general formula II:

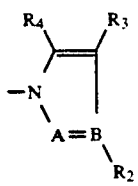

in which A and B, always different, represent a carbon atom or a nitrogen atom, the dashed line indicates the possible presence of a double bond between the 4 and 5 positions, and $R_2$, $R_3$ and $R_4$, identical or different, and can also form a part of another ring, aromatic or not, represent a hydrogen atom, a halogen, a lower alkyl radical, a nitro radical, a hydroxy radical, an alkoxy radical, a cyano radical, a carboxylic radical, a carboxamido radical, an alkyl carboxylate radical, an aryl or substituted aryl radical, a sulfonic radical, a sulfonamido radical, substituted or not on the amino group, an amino or substituted amino radical, of the general formula III:

in which $R_5$ and $R_6$, identical or different, represent a hydrogen atom, an alkyl radical, an aryl radical, an alkylcarboxy radical, an arylcarboxy radical, an alkylsulfonyl radical or an arylsulfonyl radical.

The novel derivatives of the general formula I may be prepared, according to the invention, according to any one of the following methods.

METHOD A

By the reaction of a compound of the general formula IV:

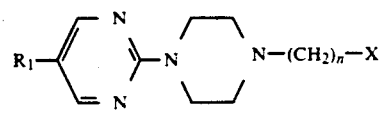

in which $R_1$ has the previously cited meanings and X represents a halogen atom, or a starting group selected from among tosyloxy or mesyloxy, with a compound of general formula V:

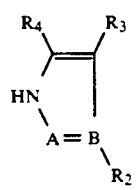

in which A, B, $R_2$, $R_3$ and $R_4$ have the previously cited meanings.

The reaction is carried out in the presence of a suitable solvent, for example dimethylsulfoxide, dimethylformamide, an alcohol, a hydrocargbon, aromatic or not, an ether, such as dioxane or diphenyl ether, or a mixture of these solvents. This reaction is advantageously conducted in the presence of a base such as hydroxides, carbonates or bicarbonates of alkali metals, or a mixture of these bases.

The most suitable temperatures vary between room temperature and the reflux temperature of the solvent, and the reaction time is comprised between 1 hour and 24 hours.

METHOD B

Method A is followed but as the reaction leads to a mixture of isomers, at the end of the reaction a separation of the components is carried out by physical methods, such as distillation, crystallizations or chromatographic methods.

METHOD C

By reduction of a compound of the general formula I, in which $R_1$, n and Het have the previously mentioned meanings and where at least one of the substituents $R_2$, $R_3$ or $R_4$, represents a nitro group.

Among the many reducing agents which can be used to reduce a nitro group to an amino group, the following may be mentioned: catalytic hydrogenation, using as catalysts nickel, palladium or platinum, zinc amalgam with hydrochloric acid, borohydrides of alkali metals, etc.

The reaction is carried out in an alcohol, such as methanol, ethanol or any one of the propanals or of butanols, or a mixture of an alcohol with water. The most suitable temperatures are comprised between −10° C. and that of the reflux of the solvent, and the reaction time is comprised between 1 hour and 24 hours.

METHOD D

By acylation of a compound of general formula I in which $R_1$, n and Het have the previously mentioned meanings and where one of the substituents $R_2$, $R_3$ or $R_4$ represents an amino group, with an acid halide or an anhydride.

The reaction is performed without solvent or in the presence of a suitable solvent, such as a hydrocarbon, a ketone or an ether, and in the presence of a base, like pyridine or the trialkylamines.

The most suitable temperatures vary between −10° C. and the boiling point of the solvent and the reaction time is comprised between 1 hour and 24 hours.

METHOD E

By alkylative reduction of a compound of the general formula I, in which $R_1$, n and Het have the previously mentioned meanings and where at least one of the substituents $R_2$, $R_3$ or $R_4$ represents a nitro group, this alkylative reduction being performed with an alkali metal borohydride in the presence of nickel chloride II and of a compound which possesses a ketone or aldehyde group. This reaction is carried out in an alcohol or a mixture of alcohol and water.

The most suitable temperatures vary between −15° C. and that of reflux of the solvent, and the reaction time is comprised between some minutes and 24 hours.

METHOD F

By reaction of a compound of the general formula I, in which $R_1$, n and Het have the previously mentioned meanings but where one at least of the substituents $R_1$ and $R_3$, represent hydrogen, with a halogen, more particularly with chlorine or bromine. This reaction can take place in a suitable solvent, such as an ether, a hydrocarbon or a halogenated hydrocarbon, like carbon tetrachloride or methylene chloride. This reaction takes place preferably at a temperature comprised between −15° C. and that of the boiling point of the solvent, and the reaction temperature is comprised between 1 hour and 24 hours.

METHOD G

By the reaction of a compound of the general formula VI:

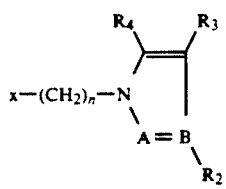

in which

A, B, $R_2$, $R_3$, $R_4$, x and n have the previously mentioned meanings, with a compound of the general formula VII:

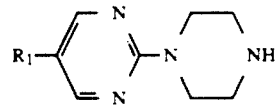

in which $R_1$ has the previously mentioned meanings.

METHOD H

By the reaction of a compound of the general formula I with an inorganic or organic acid in a suitable solvent, the corresponding salt is obtained.

In the following examples, the preparation of novel derivatives according to the invention is indicated. Also some forms of use will be described.

The Examples below, given purely by way of illustration, must not however in any case be taken as limiting the extent of the invention.

DESCRIPTION OF PREFERRED EMBODIMENTS

Method A

Example 1

Preparation of 1H-pyrazole-1-(4-(4-(2-pyrimidinyl)-1-piperazinyl)-butyl)

Under reflux for 14 hours a mixture of 4 g (13.3 mmoles) of 2-pyrimidine-1-(4-bromobutyl)-4-piperazine, 1.02 g (15 mmoles) of pyrazole and 2.76 g (20 mmoles) of potassium carbonate are heated in 50 ml of dimethylformamide. It is evaporated under vacuum, chloroform is added, it is washed with water, dried over sodium sulphate, evaporated under vacuum and 3.5 g of an oil are obtained which is 1H-pyrazole-1-(4-(4-(2-pyrimidinyl)-1-piperazinyl)-butyl).

The compounds identified by Examples 1 to 15, 31 to 37 and 43 to 48 are obtained by the same method and the data for their identification are shown in Tables I, IV, VI and VII.

Method B

Examples 25 & 26

Preparation of 1H-pyrazole-4-bromo-5-methyl-1-(4-(4-(2-pyrimidinyl)-1-piperazinyl)-butyl) and 1H-pyrazole-4-bromo-3-methyl-1-(4-(4-(2-pyrimidinyl)-1-piperazinyl)-butyl Method A is followed but with 4-bromo-3-(5)-methylpyrazole.

In this way a mixture of these two components is obtained, which are separated by high pressure preparative chromatography.

The compounds identified by Examples 23 to 30, 49 and 50 are obtained by a similar method and the data for their identification are shown in Tables III and VII.

Method C

Example 16

Preparation of 1H-pyrazole-4-amino-1-(4-(4-(2-pyrimidinyl)-1-piperazinyl)-butyl)

10.2 g (43.2 mmoles) of nickel II chloride hexahydrate are added to a solution of 7.2 g (21 mmoles) of 1H-pyrazole-4-nitro-1-(4-(4-(2-pyrimidinyl)-1-piperazinyl)-butyl Example No. 7, in 60 ml of ethanol, with vigorous shaking. It is cooled with an ice bath and slowly 10.2 g (81 mmoles) of sodium borohydride are added. It is left under stirring for 1 hour and after 1 hour at room temperature, water is added, it is evaporated under vacuum, acidified with concentrated hydrochloric acid, filtered, basified with ammonia and extracted with ethyl ether. In this way 4.4 g of 1H-pyrazole-4-amino-1-(4-(4-(2-pyrimidinyl)-1-piperazinyl)-butyl are obtained in liquid form.

The spectroscopic data for its identification are given in Table II.

Method D

Example 17

Preparation of 1H-pyrazole-4-methylsulfonamido-1-(4-(4-(2-pyrimidinyl)-1-piperazinyl)-butyl)

Slowly 1.8 g (16 mmoles) of methansulfonyl chloride are added to a cooled solution of 4.4 g (14.6 mmoles) of 1H-pyrazole-4-amino-1-(4-(4-(2-pyrimidinyl)-1-piperazinyl)-butyl, Example 16, in 30 ml of pyridine. It is left for 1 hour at 0° C., then left at room temperature for 4 hours, it is poured on iced water, extracted with chloroform and 3.7 g of 1H-pyrazole-4-methylsulfonamido-1-(4-(4-(2-pyrimidinyl)-1-piperazinyl)-butyl, which can be recrystallized in ethyl ether, with a melting point of 132° C.

The compound identified by Examples 18, 19 and 38 to 42 are obtained by the same method and the data for their identification are shown in Tables II and V.

Method E

Example 20

Preparation of 1H-pyrazole-4-(2-butyl)amino-1-(4-(4-(2-pyrimidinyl)-1-piperazinyl)-butyl 0.9 g (24 mmoles) of sodium borohydride are added to a suspension of 2.8 g (12 mmoles) of nickel dichloride hexahydrate, in a solution of 2 g (6 mmoles) of 1H-pyrazole-4-nitro-1-(4-(4-(2-pyrimidinyl)-1-piperazinyl)-butyl, Example 7, and 10 ml of methylethylketone in 50 ml of ethanol, cooled to 0° C. This temperature is maintained for 30 minutes, the temperature is allowed to rise to room temperature and the stirring continued for 2 hours; it is evaporated under vacuum, taken up again with ethyl acetate and 1.22 g of 1H-pyrazole-4-(2-butyl)amino-1-(4-(4-(2-pyrimidinyl)-1-piperazinyl)-butyl obtained, in liquid form.

The spectroscopic data of this product are shown in Table II.

Method F

Example 21

Preparation of 1H-pyrazole-4-bromo-1-(4-(4-(5-bromo-pyrimidin-2-yl)-1-piperazinyl)-butyl A solution of 1.84 g (11.5 mmoles) of bromine in 15 ml of chloroform are added slowly to a solution of 3 g (10.5 mmoles) of 1H-pyrazole-1-(4-(4-(2-pyrimidinyl)-1-piperazinyl)-butyl (Example 1). The stirring is maintained for 18 hours, it is evaporated, taken up again with a mixture of ethyl ether/benzene, basified with 10% sodium hydroxide, washed with water, dried, evaporated and 3.1 g of 1H-pyrazole-4-bromo-1-(4-(4-(5-bromopyrimidin-2-yl)-1-piperazinyl)-butyl are obtained.

The products of Examples 22, 25 and 26 are obtained by the same procedure.

The spectroscopic data for the identification of these products are shown in Tables II and III.

Method G

Example 8

Preparation of 1H-pyrazole-4-chloro-1-(4-(4-(2-pyrimidinyl)-1-piperazinyl)-butyl A mixture of 3,56 g (15 mmoles) of N-(4-bromobutyl)-4-chloropyrazol, 2.46 g (15 mmoles) of 2-(1-piperazinyl)-pyrimidine and 2.76 g (20 mmoles) of potassium carbonate in 50 ml of dimethylformamide are heated under reflux for 24 hours. It is evaporated under vacuum, chloroform added, it is washed with water, dried over sodium sulphate, evaporated under vacuum and 3.2 g of an oil obtained which is 1H-pyrazole-4-chloro-1-(4-(4-(2-pyrimidinyl)-1-piperazinyl)-butyl).

The spectroscopic data for the identification of this product are shown in Table I.

Method H

Example 52

Preparation of 1H-pyrazole-4-chloro-1-(4-(4-(2-pyrimidinyl)-1-piperazinyl)-butyl dihydrochloride 5 g of 1H-pyrazole-4-chloro-1-(4-(4-(2-pyrimidinyl)-1-piperazinyl)-butyl) are disolved in 100 ml of ethyl alcohol and heated to 60° C. By means of ethanol saturated with hydrochloric acid the solution is taken to pH 4.5-5. The resulting solution is concentrated to half its volume and it is left to crystallize at 5° C. for 12 hours. 5.5 g of crystals of melting point 194°-197.5° C. are obtained corresponding to the 1H-pyrazole-4-chloro-1-(4-(4-(2-pyrimidinyl)-1-piperazinyl)-butyl) dihydrochloride.

The product of Example 51 is obtained by the same process.

The spectroscopic data for the identification of these products are shown in Table VIII.

BIOLOGICAL ACTIVITY

The activity on the central nervous system is demonstrated for some Examples and more precisely their anxiolytic and tranquilizing action, by means of the conditioned avoidance response test, according to the method of J. S. New et cols (J. S. New, J. P. Yevich, M. S. Eison, D. P. Taylor, A. S. Eison, L. A. Riblet, C. P. Van der Maelen, D. L. Temple, *J. Med. Chem.* 1986, 29, 1476).

In this test, male Wistar rats of 200 grams weight are used, trained to jump over a barrier in an avoidance and exit cage (shuttle box) (Letica, reference L1 910 and L1 2700) in the 30 seconds following their introduction into the cage.

The products with anxiolytic or tranquilizing activity suppress the conditioned avoidance response.

Training: first day: 11 tests, at intervals of 3 minutes. Electro-shock on the paws, at 30 seconds (5 mA, 0.1 s, 10 s).

Second and third days: 2 tests per day, solely with selected rats [sum of the points of the first day (excepting the first test) > 14].

Day of test: groups formed of selected rats. Oral administration of the product or of the vehicle 45 minutes before starting the study.

In Table IX are summarized the results obtained for some products.

Taking into account their good pharmacodynamic properties, the 1H-azole-(4-(4-(2-pyrimidinyl)-1-piperazinyl)-butyl) derivatives, according to the invention, may be used satisfactorily in human and animal therapeutics, in particular in the treatment of disorders of the central nervous system, and more particularly the treatment of anxiety or as tranquilizers.

In human therapeutics, the administrative dose is of course a function of the seriousness of the disease. It will generally be comprised between about 5 and about 100 mg/day. The derivatives of the invention will be, for example, administered in the form of tablets, of solutions or suspensions, or of capsules.

There are indicated below, by way of Example, two particular galenic forms of derivatives according to the present invention.

| Example of Formula per Tablet | |
|---|---|
| Compound 1 | 5 mg |
| Lactose | 60 mg |
| Microcrystalline cellulose | 25 mg |
| Povidone | 5 mg |
| Pregelatinised starch | 3 mg |
| Colloidal silicon dioxide | 1 mg |
| Magnesium stearate | 1 mg |
| Tablet weight: | 100 mg |

| Example of Formula per Capsule | |
|---|---|
| Compound 8 | 10 mg |
| Polyoxyethylenated glyceride | 135 mg |
| Glycerine behenate | 5 mg |
| Excipient: Soft gelatine q.s. | 150 mg |

TABLE I

| Example | $R_2$ | $R_3$ | $R_4$ | n | IR cm$^{-1}$ | 1H NMR, δ, Cl$_3$ CD, J=Hz |
|---|---|---|---|---|---|---|
| 1 | H | H | H | 4 | 2942, 2815, 1586, 1547, 983 | 1.50(m, 2H); 1.90(m, 2H); 2.40(m, 6H); 3.80(m, 4H); 4.12(t, 2H, J=6.9); 6.20 (t, 1H, J=1.6); 6.40(t, 1H, J=4.7); 7.42(dd, 2H, J=4.7; J'=1.6); 8.25 (d,2H, J=4.7) |
| 2 | Me | H | Me | 4 | 1590, 1550, 1360, 1210, 980 | 1.58(m, 2H); 1.85(m, 2H); 2.20(s, 3H); 2.25(s,3H); 2.44(m, 6H); 3.81(m, 4H); 3.97(t, 2H J=7.2); 5.78(s,1H); 6.43 (t, 1H, J=4.7); 8.27(d, 2H, J=4.7) |
| 3 | Me | NO$_2$ | Me | 4 | 1590, 1550, 1350, 1260, 980 | 1.60(m, 2H); 1.90(m, 2H); 2.49(m, 9H); 2.63(s.3H); 3.82(m, 4H); 4.09(t, 2H, J= 7)6.48(t, 1H, J=4.7)8.29(d.2H.J=4.7) |
| 4 | H | Me | H | 4 | 1590, 1550, 1500, 1360, 1260, 980 | 1.52(m, 2H); 1.95(m, 2H); 2.05(s, 3H); 2.37(m.6H); 3.81(m, 4H); 4.05(t, 2H, J= 6.8); 6.41(t, 1H; J=4.7)7.13(S, 1H); 7.27(s, 1H); 8.25(d.2H, J=4.7) |
| 5 | H | —CH=CH—CH=CH— | | 4 | 2930, 1590, 1550, 1500, 1360, 1310, 1260, 980 | 1.51(m, 2H); 1.98(m, 2H); 2.36(m, 6H); 3.77(m.4H); 4.39(t, 2H, J=6.9); 6.40 (t, 1H, J=4.7); 7.0-7.7(m, 4H); 7.95 (s, 1H); 8.25(d, 2H, J=4.7) |
| 6 | Me | Br | Me | 4 | 2930, 1590, 1550, 1500, 1360, 1310, 1260, 980 | 1.55(m, 2H); 1.81(m, 2H); 2.18(s, 3H); 2.20(s,3H); 2.38(m, 4H); 3.80(m, 4H); 3.99(t, 2H, J=6.9); 6.42(t, 1H, J=4.7); 8.25(d, 2H, J=4.7) |
| 7 | H | NO$_2$ | H | 4 | 1584, 1524, 1480, 1444, 1406, 1359, 1305, 819 | 1.5(m, 2H); 1.93(m, 2H); 2.38(m, 6H); 3.76(m.4H); 4.15(t, 2H, J=6.7); 6.42 (t, 1H, J=4.7); 8.01(s, 1H)8.12(s.1H); 8.24(d, 2H, J=4.7) |
| 8 | H | Cl | H | 4 | 2843, 1586, 1547, 1358, 983 | 1.52(m, 2H); 1.90(m, 2H); 2.43(m, 6H); 3.80(m.4H); 4.0(t, 2H, J=6.8); 6.44 (t, 1H, J=4.7); 7.35(s, 1H) 7.39 (s.1H); 8.25(d, 2H, J=4.7) |
| 9 | H | EtOOC— | H | 4 | 1715, 1586, | 1.34(t, 3H, J=7.1); 1.54(m, 2H); 1.90 |

TABLE I-continued

| Example | R₂ | R₃ | R₄ | n | IR cm⁻¹ | 1H NMR. δ, Cl₃CD. J=Hz |
|---------|----|----|----|---|---------|------------------------|
|  |  |  |  |  | 1222, 983 | (m.2H); 2.46(m. 6H); 3.81(m. 4H); 4.25 (m. 4H); 6.47(t. 1H, J=4.7); 7.90 (s.2H); 8.29(d. 2H, J=4.7) |
| 10 | Me | H | Ph | 4 | 1586, 1547, 1360, 983 | 1.54(m, 2H); 1.85(m, 2H); 2.28(s.3H); 2.45(m.6H); 3.81(m, 4H); 4.07(t, 2H, J=7); 6.28(s, 1H); 6.43(t, 1H, J=4.7); 7.33(m, 4H); 7.75(m, 2H); 8.26(d, 2H, J=4.7) |
| 11 | H | Br | H | 4 | 1586, 1547, 1360, 984 | 1.52(m, 2H); 1.89(m, 2H); 2.44(m.6H); 3.62(m.4H); 4.11(t, 2H, J=6.7); 6.46 (t, 1H, J=4.6); 7.42(s, 1H); 7.45 (s, 1H); 8.29(d, 2H, J=4.6) |
| 12 | H | C≡N | H | 4 | 3076, 2231, 1587, 1551, 1258, 982 | 1.54(m, 2H); 1.96(m, 2H); 2.40(m.6H); 3.81(m.4H); 4.20(t, 2H, J=6.9); 6.48 (t, 1H, J=4.7); 7.80(s, 1H); 7.83 (s, 1H); 8.29(d, 2H, J=4.7) |
| 13 | H | F | H | 4 | 2944, 1584, 1546, 1507, 1359, 1260, 983 | 1.45(m, 2H); 1.96(m, 2H); 2.36(m.6H); 3.77(m.4H); 4.0(t, 2H, J=6.9); 6.47 (t, 1H, J=4.7); 7.27(m, 2H, J=4.8); 8.29(d, 2H, J=4.8) |
| 14 | H | Me—O— | H | 4 | 2940, 1585, 1547, 1470, 1359, 1122, 983 | 1.54(m, 2H); 1.89(m, 2H); 2.42(m.6H); 3.77(m.7H); 4.06(m, 2H); 6.42(t, 1H, J=4.7); 7.02(s, 1H) 7.26(m, 2H); 8.25 (d, 2H, J=4.6) |

TABLE II $$R_1-\text{(pyrimidine ring)}-N\overbrace{\phantom{xxx}}N-(CH_2)_n-N\overbrace{\phantom{xxx}}N-\text{(pyrazole with }R_3\text{)}$$

| Example | R₃ | R₁ | P.F. | n | IR | 1H NMR. δ, Cl₃CD. J=Hz |
|---------|----|----|------|---|----|------------------------|
| 15 | H₂N— | H | Oil | 4 | 1586, 1548 1360, 984 | 1.50(m, 2H); 1.85(m, 2H); 2.43(m, 6H); 3.4(elargie 2H); 3.8(m, 6H); 4.0 (t, 2H, J=6.4); 6.46(t, 1H, J=4.7); 6.98(s, 1H); 7.10(s, 1H); 8.27(d, 2H, J=4.7) |
| 16 | Me—SO₂—NH— | H | 132° C. | 4 | 1582, 1482 1360, 1150 983 | 1.58(m, 2H); 1.93(m, 2H); 2.45 (m, 6H); 2.94(s, 3H); 3.8(m, 4H); 4.11 (t, 2H, J=6.9); 6.45(t, 1H, J=4.7); 7.4(s, 1H); 7.5(s, 1H) 8.28(d, 2H, J=4.7) |
| 17 | Ph—CO—NH— | H | 134-6° C. | 4 | 1646, 1586 1542, 1369 | 1.55(m, 2H); 1.79(s, 3H); 1.88 (m, 2H); 2.42(m, 6H); 3.80(m, 4H); 4.13(t, 2H, J=6.8); 6.51(t, 1H, J=4.7); 7.49(m, 4H); 7.83(m, 2H); 8.0 (s, 1H); 8.11(s.1H); 8.28(d, 2H, J=4.7) |
| 18 | Me—CO—NH— | H | 80-2° C. | 4 | 1650, 1586 1454, 1364 1261, 983 | 1.50(m, 2H); 1.88(m, 2H); 2.11 (s, 3H); 2.43(m, 6H); 3.79(m, 4H); 4.08(t, 2H, J=6.8); 6.47(t, 1H, J=4.7); 7.36(s, 1H) 7.93(s, 1H); 8.28 (d, 2H, J=4.6); 9.25(s, 1H) |
| 19 | Me\CH—NH—/Et | H | Oil | 4 | 2960, 1585 1547, 1359 1260, 983 | 1.00(t, 3H, J=7.0); 1.19(d, 3H, J=6.3); 1.6(m, 4H); 1.90(m, 2H); 2.50 (m, 6H); 3.0(m, 3H); 3.9(m, 4H); 4.1 (t, 2H, J=6.8); 6.52(t, 1H, J=4.7); 6.99(s.1H); 7.17(s, 1H); 3.37 (d, 2H, J=4.7) |
| 20 | Br | Br | 84.6 | 4 | 2952, 1583 1526, 1365 1311, 950 | 1.57(m, 2H); 1.90(m, 2H); 2.45(m, 6H); 3.80(t, 4H, J=6.8); 7.44(d, 2H, J=4); 8.29(s, 2H) |
| 21 | Cl | Br | 85-6° C. | 4 | 1585, 1525 1495, 1364 | 1.50(m, 2H); 1.86(m, 2H); 2.40(m, 6H); 3.76(m, 4H); 4.08(m, 2H); 7.4 (t, 2H, J=6.9); 8.25(s, 2H) |

TABLE III

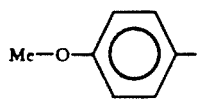

| Example | R₂ | R₃ | R₄ | n | IR cm⁻¹ | 1H NMR, δ, Cl₃CD, J=Hz |
|---|---|---|---|---|---|---|
| 22 | H | H | Me | 4 | 1585, 1550, 1500, 1450, 1360, 980 | 1.50(m, 2H); 1.80(m, 2H); 2.29(s, 3H); 2.39(m, 6H); 3.82(m, 4H); 4.04(t, 2H, J=6.9); 5.97(s, 1H); 6.40(t, 1H, J=4.7); 7.34(d, 1H, J=2.1); 8.24(d, 2H, J=4.7) |
| 23 | Me | H | H | 4 | 1585, 1550, 1500, 1450, 1360, 980 | 1.52(m, 2H); 1.81(m, 2H); 2.25(s,3H); 2.44(m,6H); 3.81(m, 4H); 4.03(t, 2H, 5.95(s, 1H)6.42(t, 1H, J=4.7); 7.23 (d, 1H, J=2.1); 8.27(d, 2H, J=4.7) |
| 24 | H | Br | Me | 4 | 1590, 1550, 1500, 1450, 1360, 1260, 980 | 1.52(m, 2H); 1.83(m, 2H); 2.26(s,3H); 2.45(m,6H); 3.80(m, 4H); 6.45(t, 1H, J=4.7); 7.38(d, 1H, J=1.8); 8.27 (d, 2H, J=4.7) |
| 25 | Me | Br | H | 4 | 1590, 1550, 1500, 1450, 1360, 1260, 980 | 1.53(m, 2H); 1.84(m, 2H); 2.22(s,3H); 2.45(m,6H); 3.80(m, 4H); 6.46(t, 1H, J=4.7); 7.31(d, 1H, J=1.7); 8.29 (d, 2H, J=4.7) |
| 26 | H | —(CH₂)₄— | | 4 | 2930, 1590, 1550, 1500, 1450, 1360, 1310, 1260, 980 | 1.70(m, 8H); 2.45(m, 10H); 3.8(m,4H); 4.04(t, 2H, J=6.9); 6.43(t, 1H, J=4.7); 7.23(d, 1H, J=1.8); 8.26(d, 2H, J=4.7) |
| 27 | —(CH₂)₄— | | H | 4 | 2930, 1590, 1550, 1500, 1450, 1360, 1310, 1260, 980 | 1.70(m, 8H); 2.45(m, 10H); 3.8(m,4H); 3.97(t, 2H, J=6.9); 6.45(t, 1H, J=4.7); 7.05(d, 1H, J=1.8); 8.27(d, 2H, J=4.7) |
| 28 | H | Ph | Me | 4 | 1590, 1550, 1500, 1450, 1360, 1310, 1260, 980 | 1.50(m, 2H); 1.90(m, 2H); 2.39(s,3H); 2.50(m,6H); 3.80(m, 4H); 4.1(t, 2H, J=6.9); 6.44(t, 1H, J=4.7); 7.35 (m, 6H); 8.27(d, 2H, J=4.7) |
| 29 | Me | Ph | H | 4 | 1590, 1550, 1500, 1450, 1360, 1310, 1260, 980 | 1.50(m, 2H); 1.90(m, 2H); 2.40(s,3H); 2.51(m,6H); 3.81(m, 4H); 4.09(t, 2H, J=6.9); 6.44(t, 1H, J=4.7); 7.34 (m, 6H); 8.28(d, 2H, J=4.7) |

TABLE IV

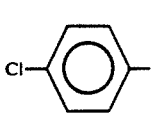

| Example | R₂ | R₃ | R₄ | IR cm⁻¹ | 1H NMR, δ, Cl₃CD, J=Hz |
|---|---|---|---|---|---|
| 30 | Cl | F | H | 2944, 1585, 1547, 1507, 1360, 1260, 984 | 1.52(m, 2H); 1.90(m, 2H); 2.40(m, 6H); 3.80(m, 4H); 4.0(t, 2H, J=4.8); 6.45 (t, 1H, J=4.7); 7.30(d, 1H, J=4.8); 8.29 d, 2H, J=4.8) |
| 31 | Cl | Me—O | H | 2940, 1586, 1470, 1360, 1121, 983 | 1.53(m, 2H); 1.90(m, 2H); 2.4(m, 6H); 3.8(m,7H); 4.0(m, 2H); 6.4(t, 1H, J=4.8); 7.0(s, 1H); 7.25(s, 1H); 8.2(d, 2H, J=4.8) |
| 32 | H | Me—O—⌬— | H | 2390, 1589, 1545, 1495, 1360, 1247, 983, 835, 799 | 1.62(m, 2H); 1.88(m, 2H); 2.45(m,6H); 3.81(m, 7H); 4.16(t, 2H, J=6.8); 6.46 (t, 1H, J=4.7); 6.9(d, 2H, J=4.4); 7.4 (d, 2H, J=4,4); 7.55(s, 1H); 7.7(s, 1H) 8.28(d, 2H, J=2,4) |
| 33 | H | Cl—⌬— | H | 2946, 1586, 1549, 1485, 1395, 1257, 982, 951, 830 | 1.6(m, 2H); 1.9(m, 2H); 2.46(m, 6H); 3.8(m,4H); 4.16(t, 2H, J=6.8); 6.4 (t, 1H, J=4.7); 7.36(d, 4H, J=1,3); 7.7(d, 2H, J=6,2); 8.28(d, 2H, J=2,3) |

TABLE IV-continued

Structure: pyrimidine-N-piperazine-N-(CH₂)₄-N-N=C(R₂) with R₃, R₄ on adjacent C

| Example | R₂ | R₃ | R₄ | IR cm⁻¹ | 1H NMR. δ. Cl₃ CD. J=Hz |
|---|---|---|---|---|---|
| 34 | H | -N(pyrrolyl) | H | 2943, 1586, 1487, 1359, 1260, 984, 726 | 1.55(m, 2H); 1.80(m, 2H); 2.45(m, 6H); 3.81(t, 4H, J=5); 4.12(t, 2H, J=7); 6.25(2H, t, J=2); 6.44(1H, t, J=4,7); 6.84(m, 2H); 7.5(d, 2H, J=5); 8.27 (d, 2H, J=4,7) |
| 35 | H | phenyl | H | 2942, 1585, 1493, 1446, 1359, 1258, 983, 760 | 1.6(m, 2H); 1.9(m, 2H); 2.5(m, 4H); 3.8(m, 6H); 4.2(t, 2H, J=6,8)6.7(t, 1H, J=4,7); 7.2-7.7(abs. compl. 5H); 8.0 (s, 1H); 8.2(s, 1H); 8.4(d, 2H, J=2,3) |
| 36 | phenyl | H | phenyl | 2942, 1585, 1547, 1485, 1359, 1260, 983, 763, 697 | 1.6(m, 2H); 1.9(m, 2H); 2.35(m, 6H); 3.8(m, 4H); 4.2(t, 2H, J=6.8); 6.4 (t, 1H, J=4,7); 6.6(s, 1H); 7.2-7.4 (abs. compl. 8H); 7.8(m, 2H); 8.25 (d, 2H, J=2,4) |

TABLE V

Structure: pyrimidine-N-piperazine-N-(CH₂)₄-N-N=CH with R₃

| Example | R₃ | IR cm⁻¹ | 1H NMR. δ. Cl₃ CD. J=Hz |
|---|---|---|---|
| 37 | phenyl-SO₂-NH- | 2931, 1584, 1548, 1490, 1358, 1167, 983 | 1.45(m, 2H); 1.85(m, 2H); 2.40(m, 6H); 3.80(m, 4H); 4.0(t, 2H, J=6,7); 6.47 (t, 1H, J=4.6); 7.0(s, 1H); 7.5(m, 6H); 8.3(d, 2H, J=4.6) |
| 38 | Me-phenyl-SO₂-NH | 2943, 1585, 1548, 1446, 1360, 1161, 984 | 1.5(m, 2H); 1.85(m, 2H); 2.28(m, 9H); 3.8(m, 4H); 4.0(m, 2H); 6.45(t, 1H, J=4,7); 7-7.65(m, 6H); 8.27(d, 2H, J=4,7) |
| 39 | n-Bu-SO₂-NH- | 2941, 1586, 1548, 1448, 1360, 1146, 984, 755 | 0.91(t, 3H, J=6,8); 1.45(m, 4H); 1.85 (m, 4H); 2.40(m, 6H); 3.0(m, 2H); 3.80(m, 4H); 4.11(t, 2H, J=6,5); 6.5(t, 1H, J=4,7); 7.4(m, 2H); 7.5 (s, 1H); 8.3(d, 2H, J=4,7) |
| 40 | n-Pr-SO₂-NH- | 2940, 1586, 1548, 1447, 1360, 1146, 984, 755 | 1.0(t, 3H, J=7.1); 1.55(m, 2H); 1.9 (m, 4H); 2.45(m, 6H); 3.0(t, 2H, J=7.4); 3.8(m, 4H); 4.1(t, 2H, J=6,4); 6.46(t, 1H, J=4,7); 7.35(m, 2H); 7.5 (s, 1H); 8.3(d, 2H, J=4,7) |
| 41 | Et-SO₂-NH- | 2943, 1586, 1548, 1447, 1360, 1146, 984, 754 | 1.36(m, 5H); 1.9(m, 2H); 2.45(m, 6H); 3.0(m, 2H); 3.6(m, 4H); 4.1(t, 2H, J=6,4); 6.45(t, 1H, J=4,7); 7.39 (s, 1H); 7.51(s, 1H); 8.3(d, 2H, J=4,7) |

TABLE VI

Structure: pyrimidine-N-piperazine-N-(CH₂)₄-N-N=C(R₂) with R₃, R₄

| Example | R₂ | R₃ | R₄ | IR cm⁻¹ | 1H NMR. δ. Cl₃ CD. J=Hz |
|---|---|---|---|---|---|
| 42 | Me | -SO₂-N-Me₂ | Me | 2939, 1586, | 1.7(m, 4H); 2.3-3.0(abs. compl. 18H); |

TABLE VI-continued

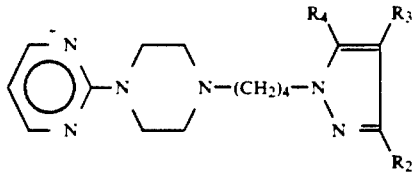

| Example | R2 | R3 | R4 | IR cm$^{-1}$ | 1H NMR, δ, Cl3 CD, J=Hz |
|---|---|---|---|---|---|
| | | | | 1547, 1448, 1360, 1290, 983, 951, 788 | 3.8(m, 4H); 4.0(t, 2H, J=6.8); 6.5 (t, 1H, J=4,7); 8.2(d, 2H, J=2,35) |
| 43 | H | —SO2—N—Me2 p.f. 100-2° C. | H | 3135, 2943, 1586, 1512, 1357, 1328, 1156, 982, 728 | 1.6(m, 2H); 1.9(m, 2H); 2.3-2.7(abs. compl. 13H); 3.8(m, 4H); 4.2(t, 2H, J=6,8); 6.4(t, 1H, J=4,7); 7.75(d, 1H, J=4,4); 8.28(d, 2H, J=2,4) |
| 44 | H | —SO3—H p.f. 235° C. | H | 3330, 1590, 1556, 1449, 1220, 1178, 1049, 971, 656 | 1.95(m, 2H); 3.3(m, 6H); 4.0(s, 5H); 4.27(t, 2H, J=6,1); 6.8(t, 1H, J=4,8); 7.8(s, 1H); 8.0(s, 1H); 8.43(d, 2H, J=2,4) |

TABLE VII

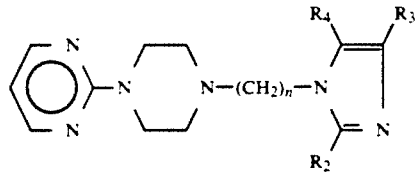

| Example | R2 | R3 | R4 | n | IR cm$^{-1}$ | 1H NMR, δ, Cl3 CD, J=Hz |
|---|---|---|---|---|---|---|
| 45 | H | H | H | 4 | 2940, 1585, 1500, 1360, 1260, 975, | 1.6(m, 2H); 1.8(m, 2H); 2.5(m, 6H); 3.80(m, 6H); 6.5(t, 1H, J=4,7); 6.9 (s, 1H); 7.1(s, 1H); 7.5(s, 1H); 8.4 (d, 2H, J=4,7) |
| 46 | H | Cl | Cl | 4 | 2946, 1584, 1543, 1492, 1359, 1254, 983, 797 | 1.4-2.1(abs. compl. 4H); 2.46(m, 6H); 3.86(m, 6H); 6.47(t, 1H, J=4,7); 7.38(s, 1H); 8.29(d, 2H, J=4,7) |
| 47 | H | Me | H | 4 | 2942, 1585, 1548, 1447, 1359, 1260, 984, 735 | 1.4-2.0(abs. compl. 4H); 2.21(s, 3H); 2.45(m.6H); 3.82(m, 6H); 6.47(t, 1H, J=4,7); 6.62(s, 1H); 7.35(s, 1H); 8.28 (d, 2H, J=4,7) |
| 48 | H | H | Me | 4 | 2942, 1585, 1548, 1446, 1359, 1260, 984, 736 | 1.4-2.0(abs. compl. 4H); 2.20(s, 3H); 2.45(m.6H); 3.82(m, 6H); 6.47(t, 1H, J=4,7); 6.79(s, 1H); 7.40(s, 1H); 8.28 (d, 2H, J=4,7) |

TABLE VIII

| Example | X | M.P. °C. | IR cm$^{-1}$ |
|---|---|---|---|
| 49 | 1 HCl | 156-8 | 3490, 1592, 1556, 1481, 1438, 1386, 970 |
| 50 | 2 HCl.H2O | 194-197.5 | 3429, 2688, 1636, 1620, 1346, 1218, 971 |

TABLE IX

| Example | Activity % | ED50 (mg/kg) |
|---|---|---|
| 1 | 98 | 26.2 |
| 2 | 50 | 80.0 |
| 3 | 61 | 58.3 |
| 4 | 98 | <20.0 |
| 5 | 45 | 80.0 |
| 6 | 51 | 80.0 |
| 7 | 98 | 6.2 |
| 8 | 95 | 17.9 |
| 9 | 14 | — |
| 10 | 24 | — |
| 11 | 95 | 28.9 |
| 12 | 100 | — |
| 13 | 85 | — |
| 15 | 79 | 27.7 |
| 16 | 64 | 40.0 |
| 17 | 62 | 65.9 |
| 18 | 89 | 28.8 |
| 19 | 80 | 29.7 |
| 20 | 59 | 76.8 |
| 21 | 48 | 51.7 |
| 22 | 47 | — |
| 24 | 53 | 60.6 |
| 25 | 59 | 58.3 |
| 26 | 97 | 19.5 |
| 27 | 98 | 18.9 |

TABLE IX-continued

| Example | Activity % | ED$_{50}$ (mg/kg) |
|---|---|---|
| 28 | 75 | 32.2 |
| 29 | 78 | 31.9 |
| 30 | 85 | 53.9 |
| 32 | 60 | 22.5 |
| 33 | 90 | 15.7 |
| 34 | 100 | 5 |
| 35 | 100 | 27.4 |
| 36 | 31 | 122 |
| 37 | 46 | 85 |
| 38 | 37 | 102 |
| 39 | 57 | 73 |
| 40 | 57 | 73 |
| 41 | 77 | 29.3 |
| 42 | 45 | 82 |
| 43 | 63 | 72 |
| 44 | 15 | — |
| 45 | 35 | 93 |
| 46 | 99 | — |
| 47 | 50 | 80 |
| 48 | 52 | 75 |
| 49 | 100 | 14.5 |
| 50 | 99 | 4.9 |
| Buspirone | 99 | 17.2 |
| Ipsapirone | 98 | 26.1 |

We claim:

1. Heterocyclic compounds corresponding to the formula I:

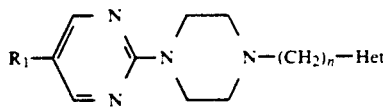

in which R$_1$ represents a hydrogen atom or a halogen, n has the values 1 to 6 and Het represents an azole, or one of its derivatives selected from the group consisting of imidazole, indazole, tetrahydroindazoles and pyrazole and which is represented by the formula II:

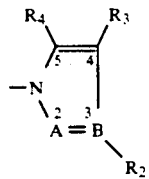

in which A and B, always different, represent carbon or nitrogen and R$_2$, R$_3$ and R$_4$, identical or different, and which can also form a part of another ring having up to 4 additional carbon atoms represent hydrogen, halogen, lower alkyl, nitro, hydroxy alkoxy, cyano, carboxylic, carboxamido, alkyl carboxyalate, phenyl, substituted phenyl having a single substituent of the class consisting of methoxy and chlorine, sulfonic, sulfonamido having 1 to 2 methyl substituents on the amino group, or an amino radical, of formula III:

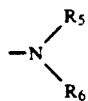

in which R$_5$ and R$_6$, identical or different, represent hydrogen, alkyl having up to 4 carbon atoms, methylcarboxy, phenylcarboxy, alkylsulfonyl having 1 to 4 carbon atoms in its alkyl group or phenylsulfonyl.

2. The compounds corresponding to the formula I according to claim 1, selected from the group consisting of 1—1H-pyrazole-1-(4-(4-(2-pyrimidinyl)-1-pipérazinyl)-butyl),
2—1H-pyrazole-3,5-diméthyl-1-(4-(4-(2-pyrimidinyl)-1-pipérazinyl)-butyl),
3—1H-pyrazole-3,5-diméthyl-4-nitro-1-(4-(4-(2-pyrimidinyl)-1-pipérazinyl-butyl),
4—1H-pyrazole-4-méthyl-1-(4-(4-(2-pyrimidinyl)-1-pipérazinyl)-butyl),
5—1H-indazole-1-(4-(4-(2-pyrimidinyl)-1-pipérazinyl)-butyl),
6—1H-pyrazole-3,5-diméthyl-4-bromo-1-(4-(4-(2-pyrimidinyl)-1-pipérazinyl)-butyl),
7—1H-pyrazole-4-nitro-1-(4-(4-(2-pyrimidinyl)-1-pipérazinyl)-butyl),
8—1H-pyrazole-4-chloro-1-(4-(4-(2-pyrimidinyl)-1-pipérazinyl)-butyl),
9—1H-pyrazole-4-ethylcarboxylate-1-(4-(4-(2-pyrimidinyl)-1-pipérazinyl)-butyl),
10—1H-pyrazole-3-méthyl-5-phényl-1-(4-(4-(2-pyrimidinyl)-1-pipérazinyl)-butyl),
11—1H-pyrazole-4-bromo-1-(4-(4-(2-pyrimidinyl)-1-pipérazinyl)-butyl),
12—1H-pyrazole-4-cyano-1-(4-(4-(2-pyrimidinyl)-1-pipérazinyl)-butyl),
13—1H-pyrazole-4-fluoro-1-(4-(4-(2-pyrimidinyl)-1-pipérazinyl)-butyl),
14—1H-pyrazole-4-méthoxy-1-(4-(4-(2-pyrimidinyl)-1-pipérazinyl)-butyl),
15—1H-pyrazole-4-amino-1-(4-(4-(2-pyrimidinyl)-1-pipérazinyl)-butyl),
16—1H-pyrazole-4-méthylsulfonamido-1-(4-(4-(2-pyrimidinyl)-1-pipérazinyl)-butyl),
17—1H-pyrazole-4-benzamido-1-(4-(4-(2-pyrimidinyl)-1-pipérazinyl)-butyl),
18—1H-pyrazole-4-acétamido-1-(4-(4-(2-pyrimidinyl)-1-pipérazinyl)-butyl),
19—1H-pyrazole-4-(2-butyl)amino-1-(4-(4-(2-pyrimidinyl)-1-pipérazinyl)-butyl),
20—1H-pyrazole-4-bromo-1-(4-(4-(5-bromopyrimidin-2-yl)-1-pipérazinyl)-butyl),
21—1H-pyrazole-4-bromo-1-(4-(4-(5-chloropyrimidin-2-yl)-1-pipérazinyl)-butyl),
22—1H-pyrazole-5-méthyl-1-(4-(4-(2-pyrimidinyl)-1-pipérazinyl)-butyl),
23—1H-pyrazole-3-méthyl-1-(4-(4(2-pyrimidinyl)-1-pipérazinyl)-butyl,
24—1H-pyrazole-4-bromo-5-méthyl-1-(4-(4-(2-pyrimidinyl)-1-pipérazinyl)-butyl),
25—1H-pyrazole-4-bromo-3-méthyl-1-(4-(4-(2-pyrimidinyl)-1-pipérazinyl)-butyl)
26—1H-4,5,6,7-tétrahydroindazole-1-(4-(4-(2-pyrimidinyl)-1-pipérazinyl)-butyl),
27—2H-3,4,5,6-tétrahydroindazole-2-(4-(4-(2-pyrimidinyl)-1-pipérazinyl)-butyl),
28—1H-pyrazole-5-méthyl-4-phényl-1-(4-(4-(2-pyrimidinyl)-1-pipérazinyl)-butyl),
29—1H-pyrazole-3-méthyl-4-phényl-1-(4-(4-(2-pyrimidinyl)-1-pipérazinyl)-butyl),
30—1H-pyrazole-3-chloro-4-fluoro-1-(4-(4-(2-pyrimidinyl)-1-pipérazinyl)-butyl),
31—1H-pyrazole-3-chloro-4-méthoxy-1-(4-(4-(2-pyrimidinyl)-1-pipérazinyl)-butyl), 32—1H-pyrazole-4-(4-méthoxyphényl)-1-(4-(4-(2-pyrimidinyl)-1-pipérazinyl)-butyl),
33—1H-pyrazole-4-(4-chlorophényl)-1-(4-(4-(2-pyrimidinyl)-1-pipérazinyl)-butyl),
34—1H-pyrazole-4-(1-pyrrolyl)-1-(4-(4-(2-pyrimidinyl)-1-pipérazinyl)-butyl)
35—1H-pyrazole-4-phényl-1-(4-(4-(2-pyrimidinyl)-1-pipérazinyl)-butyl),
36—1H-pyrazole-3,5-diphényl-1-(4-(4-(2-pyrimidinyl)-1-pipérazinyl)-butyl),
37—1H-pyrazole-4-phénylsulfonamido-1-(4-(4-(2-pyrimidinyl)-1-pipérazinyl)-butyl),
38—1H-pyrazole-4-(4-méthylbenzene)sulfonamido-1-(4-(4-(2-pyrimidinyl)-1-pipérazinyl)-butyl),
39—1H-pyrazole-4-butylsulfonamido-1-(4-(4-2-pyrimidinyl)-1-pipérazinyl)-butyl),
40—1H-pyrazole-4-propylsulfonamido-1-(4-(4-(2-pyrimidinyl)-1-pipérazinyl)-butyl),
41—1H-pyrazole-4-ethylsulfonamido-1-(4-(4-(2-pyrimidinyl)-1-pipérazinyl)-butyl),
42—1H-pyrazole-3,5-diméthyl-4-(N,N-dimethylsulfonamido)-1-(4-(4-(2-pyrimidinyl)-1-pipérazinyl)-butyl),
43—1H-pyrazole-4-N-dimethylsulfonamido-1-(4-(4-(2-pyrimidinyl)-1-piperazinyl)-butyl,
44—1H-pyrazole-4-sulfonique-1-(4-(4-(2-pyrimidinyl)-1-pipérazinyl)-butyl),
45—1H-imidazole-1-(4-(4-(2-pyrimidinyl)-1-pipérazinyl)-butyl),
46—1H-imidazole-4,5-dichloro-1-(4-(4-(2-pyrimidinyl)-1-pipérazinyl)-butyl),
47—1H-imidazole-4-méthyl-1-(4-(4-(2-pyrimidinyl)-1-pipérazinyl)-butyl),
48—1H-imidazole-5-méthyl-1-(4-(4-(2-pyrimidinyl)-1-pipérazinyl)-butyl),
49—1H-pyrazole-4-chloro-1-(4-(4-(2-pyrimidinyl)-1-pipérazinyl)-butyl) hydrochlorure,
50—1H-pyrazole-4-chloro-1-(4-(4-(2-pyrimidinyl)-1-pipérazinyl)-butyl) dihydrochlorure.

3. Pharmaceutical compositions comprising besides a pharmaceutically acceptable support, at least one derivative of the formula I or one of its physiologically acceptable salts, according to claim 1.

4. Method of treating anxiety in human or animal patients, comprising administering to said patients a derivative of the formula I, according to claim 1 and/or a physiologically acceptable salt thereof.

* * * * *